(12) United States Patent
Hwang et al.

(10) Patent No.: US 8,367,726 B2
(45) Date of Patent: Feb. 5, 2013

(54) ACID SALT OF TOLTERODINE HAVING EFFECTIVE STABILITY FOR TRANSDERMAL DRUG DELIVERY SYSTEM

(75) Inventors: Yong Youn Hwang, Suwon-si (KR); Nam Ho Kim, Yongin-Si (KR); Won Jae Choi, Seoul (KR); Yong Han Kim, Gyeonggi-do (KR)

(73) Assignee: SK Chemicals Co., Ltd., Gyeonggi-Do (KR)

( * ) Notice: Subject to any disclaimer, the term of this patent is extended or adjusted under 35 U.S.C. 154(b) by 69 days.

(21) Appl. No.: 12/918,753

(22) PCT Filed: Feb. 20, 2009

(86) PCT No.: PCT/KR2009/000814
§ 371 (c)(1),
(2), (4) Date: Aug. 26, 2010

(87) PCT Pub. No.: WO2009/104920
PCT Pub. Date: Aug. 27, 2009

(65) Prior Publication Data
US 2010/0331552 A1 Dec. 30, 2010

(30) Foreign Application Priority Data
Feb. 20, 2008 (KR) .................. 10-2008-0015336

(51) Int. Cl.
*A01N 37/30* (2006.01)
*A61K 31/205* (2006.01)

(52) U.S. Cl. .................. 514/555; 564/316; 562/490

(58) Field of Classification Search .................. 514/555; 562/490; 564/316
See application file for complete search history.

(56) References Cited

U.S. PATENT DOCUMENTS

| 5,382,600 A | 1/1995 | Jonsson et al. |
| 5,559,269 A | 9/1996 | Johansson et al. |
| 7,005,449 B2 * | 2/2006 | Hawley et al. ............... 514/555 |
| 2003/0199582 A1 | 10/2003 | Hawley et al. |

FOREIGN PATENT DOCUMENTS

| WO | WO 98/29402 A | 7/1998 |
| WO | WO 00/12070 A | 3/2000 |
| WO | WO 02/34245 A | 5/2002 |

OTHER PUBLICATIONS

Postlind, Hans et al.: "Tolterodine, A New Muscarinic Receptor Antagonist, is Metabolized by Cytochromes P450 2D6 and 3A in Human Liver Microsomes", *Drug Metab Discocs*, Apr. 1998:28(4):269-93.

* cited by examiner

*Primary Examiner* — Yong Chu
*Assistant Examiner* — Valerie Rodriguez-Garcia
(74) *Attorney, Agent, or Firm* — Frommer Lawrence & Haug LLP; Ronald R. Santucci

(57) ABSTRACT

The present invention relates to an acid salt of tolterodine with superior stabililty and useful as a transdermal drug delivery system. More specifically, the present invention relates to a novel acid salt of tolterodine with superior stabililty to the conventional acid salts of tolterodine, which is useful as a pharmaceutical composition for the treatment of overactive bladder and can be formulated into a transdermal drug delivery system.

3 Claims, No Drawings

ACID SALT OF TOLTERODINE HAVING EFFECTIVE STABILITY FOR TRANSDERMAL DRUG DELIVERY SYSTEM

This application is a 371 of PCT/KR2009/000814 filed on Feb. 20, 2009 published on Aug. 27, 2009 under publication number WO 2009/104920 A which claims priority benefits to Korean Patent Application Number 10-2008-0015336 filed Feb. 20, 2008, the disclosure of which is incorporated herein by reference.

TECHNICAL FIELD

The present relates to an acid salt of tolterodine with superior stabililty and useful as a transdermal drug delivery system.

BACKGROUND ART

U.S. Pat. No. 5,382,600 discloses that (substituted) 3,3-diphenylpropylamine is effective for the treatment of overactive bladder. In particular, the above patent teaches that 2-[(1R)-3-(diisopropylamino)-1-phenylpropyl)-4-methylphenol, which has a general name of tolterodine [formula 1] and has been known as N,N-diisopropyl-3-(2-hydroxy-5-methylphenyl)-3-phenylpropylamine, is useful for the treatment of overactive bladder. Tolterodine is a compound disclosed in Example 22 of U.S. Pat. No. 5,382,600. Tolterodine is preferably manufactured by a method disclosed in WO Publication No. 98/29402.

H. Postlind et al. reported that tolterodine is a Muscarinic receptor antagonist [Drug Metabolism and Disposition, 26(4): 289-293 (1998)]. It has been on the commercial market as Detrol (Pharmacia). Tolterodine is orally administered in the form of a tablet for the treatment of overactive bladder. Active metabolites of tolterodine are hydroxytolterodines.

U.S. Pat. No. 5,559,269 and H. Postlind et al. disclosed hydroxytolterodine [Drug Metabolism and Disposition, 26(4): 289-293 (1998)].

U.S. Pat. No. 5,559,269 teaches that the above compound is effective in the treatment of overactive bladder, and it has been reported that hydroxytolterodine has an anti-muscarine property [Pharmacol. Toxicol., 81: 169-172 (1997)].

WO Publication No. 98/29402 discloses tolterodine salts of methane sulfonic acid, hydrochloric acid, hydrobromic acid, sulfuric acid, phosphoric acid, nitric acid, benzoic acid, citric acid, tartaric acid, fumaric acid, maleic acid, $CH_3$—$(CH_2)$n-COOH (here, n is an integer of 0-4), HOOC—$(CH_2)$n-COOH (here, n is an integer of 0-4).

WO Publication No. 02/34245 discloses the uses of tolterodine as a treatment for asthma, COPD and allergic nasal inflammation.

Tolterodine, a commercial therapeutic agent for the treatment of overactive bladder, is administered in the form of a film-coated tablet comprising 1 mg, 2 mg or 4 mg of tolterodine L-tartrate to be released in the gastrointestinal tract. With regard to drugs, customers have always asked a selective delivery form to improve the quality of their lives such as excellent efficacies and/or convenient treatment.

'Overactive bladder' a newly coined medical term, refers to a physical condition with symptoms of urinary frequency, urinary urgency or urgent urinary incontinence.

'Urinary frequency' refers to a condition of a person having urination more than 8 times daily, and it may accompany a desire for urination even after urination.

'Urinary urgency' refers to a condition of a person when urination cannot be endured any more and thus urgent urination is required.

'Urgent urinary incontinence' refers to a condition of a person when urine is being leaked out due to sudden intolerable urination desire.

About more than 50 million people around the world suffer from 'Overactive bladder' About 22% of adults aged 40 or older have the overactive bladder symptom. It develops in practically both males and females in all age groups but more frequently in females. It is caused by extremely frequent contraction of detrusor muscle, the smooth muscle of overactive bladder. That is, the bladder muscle contracts more frequently than normal or contracts when not necessary thereby giving out a sudden signal for urination. The major cause in most cases has not been yet identified but in some patients it appears to be due to the defect in neurotransmission or neuronal damage resulted from surgery or baby delivery. In case of men, it is very common to have both prostatic hypertrophy and overactive bladder.

Overactive bladder is a disease that often accompanies lack of sleep, decrease in work efficiency, avoidance of sexual life, depression and social phobia resulted from lack of information and a sense of shame on the disease, thus greatly lowering the quality of life. The correlation between the diseases including overactive bladder and quality of life was investigated and the result (SF-36 Questionnaire) showed that overactive bladder decreases the quality of life further as compared to other adult diseases such as diabetes and hypertension. Therefore, there is an urgent need for the development of a novel pharmaceutical compound to restore the quality of life of the overactive bladder patients.

From the pharmacological point of view, tolterodine (formula 1) is preferred to be in a free base form. However, it is very hard to handle during the manufacturing process because it is in a liquid form with high viscosity thus lowering the yield, and has poor storage stability and thus it is generally administered in the form of an acid salt with a pharmaceutically acceptable acid.

The acid salt of tolterodine currently used for the treatment of overactive bladder is tolterodine tartrate (formula 2)

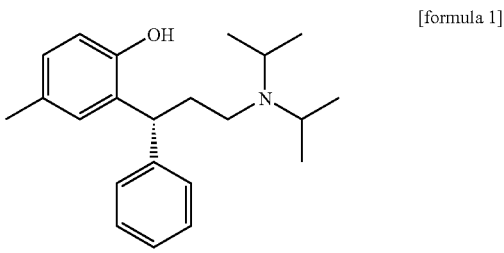

[formula 1]

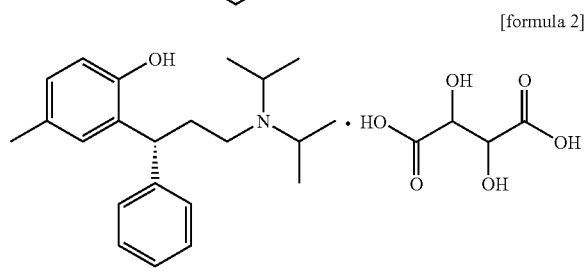

[formula 2]

Korean Pat. No. 90,479 discloses that a pharmaceutically acceptable salt should meet the following four physicochemical requirements: (1) excellent solubility (2) excellent storage stability (3) non-hygroscopicity (4) processability into tablets. However, it is not easy for a pharmaceutically acceptable salt to meet all the above listed conditions. In fact, even tolterodine tartrate decomposes itself within a few weeks when placed in a solution thus posing a stability problem. Further, its transdermal absorption rate is much lower than that of tolterodine free base form.

DISCLOSURE OF INVENTION

Technical Problem

The inventors of the present invention have studied various novel acid salts of tolterodine prepared from the liquid amorphous tolterodine free base, and methods for transdermal delivery of these novel pharmaceutical compounds by various formulation methods. As a result, they have succeeded in manufacturing various acid salts of tolterodine in an efficient and cost-effective manner. Further, for some of the above novel pharmaceutical compounds, the inventors have developed a novel method for the transdermal delivery of the novel pharmaceutical compounds, which were found to be more useful than the conventional tolterodine tartrate in terms of drug delivery, by using pharmaceutical technologies.

Therefore, an object of the present invention is to provide various acid salts of tolterodine which was prepared from liquid amorphous tolterodine free base.

Another object of the present invention is to provide a method for transdermal delivery of the above novel pharmaceutical compounds using pharmaceutical technologies.

A further object of the present invention is to provide a pharmaceutical composition for the treatment of overactive bladder comprising the above novel pharmaceutical compounds as active ingredients.

Technical Solution

The present invention relates to novel acid salts of tolterodine which have improved storage stability than the conventional tolterodine tartrate and also can be formulated into a transdermal drug delivery system.

BEST MODE FOR CARRYING OUT THE INVENTION

The present invention is described further in details as set forth hereunder.

The present invention, as essential requirements for various acid salts of tolterodine, noted that the transdermal absorption of the conventional tolterodine tartrate is much lower than that of tolterodine free base, and as a result selected hippuric acid, adipic acid, gentisic acid, benzenesulfonic acid, p-toluenesulfonic acid, L-pyroglutamic acid, benzoic acid, naphthalene-1,5-disulfonic acid, 1-hydroxy-2-naphthoic acid, glycolic acid, retinoic acid, and prepared various acid salts of tolterodine by using the above 11 different acids.

The manufacturing method varies a little depending on the acid salt.

Various acid salts of tolterodine can be prepared by mixing tolterodine free base with an acid in an equivalent ratio of 1.0:0.1~2.0, stirring the mixture in the presence of a polar organic solvent (ethylacetate, acetone, methanol, ethanol, isopropanol, t-butanol, dichloromethane, chloroform, toluene, tetrahydrofuran, etc.) for 1-24 hr; or adding a nonpolar organic solvent (hexane, heptane, octane, diethylether, etc.) thereto and stirring; or evaporating under reduced pressure of an organic solvent (ethylacetate, acetone, methanol, ethanol, isopropanol, t-butanol, dichloromethane, chloroform, toluene, tetrahydrofuran, hexane, heptane, octane, diethylether, etc.). These methods are already well known to the skilled person in the art.

[formula 3: tolterodine hippurate]

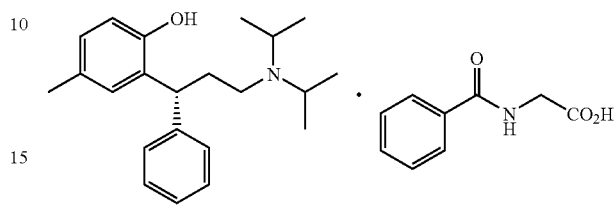

[formula 4: tolterodine hemiadipate]

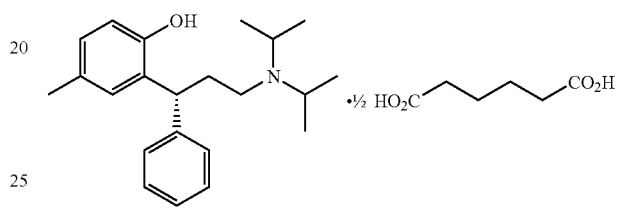

[formula 5: tolterodine gentisate]

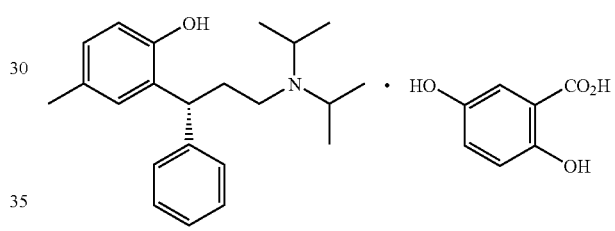

[formula 6: tolterodine benzene sulfonate]

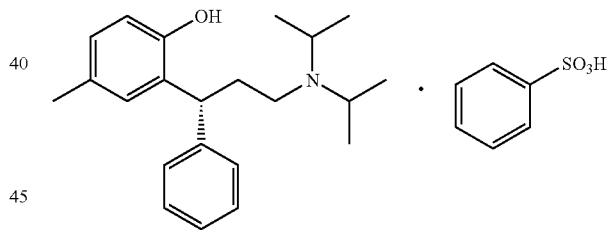

[formula 7: tolterodine p-toluene sulfonate]

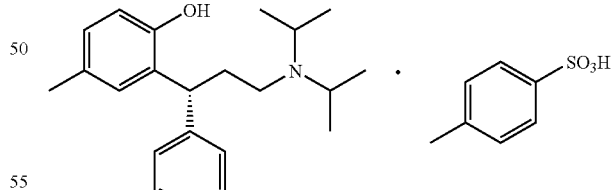

[formula 8: tolterodine L-pyroglutamate]

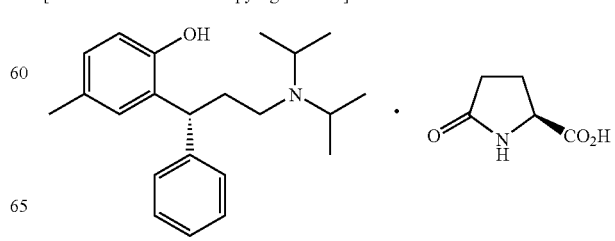

-continued

[formula 9: tolterodine benzoate]

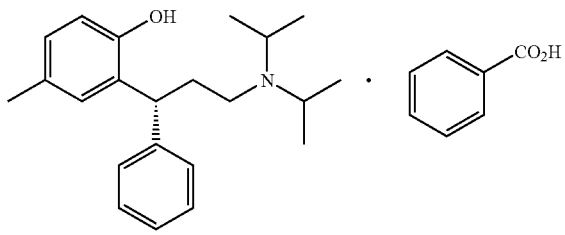

[formula 10: tolterodine hemi naphthalene-1,5-disulfonate]

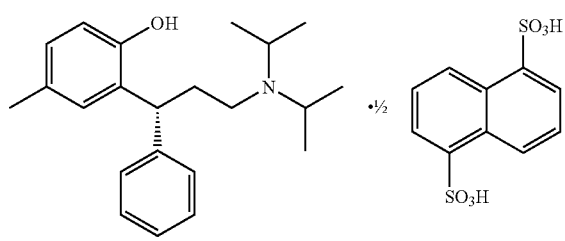

[formula 11: tolterodine 1-hydroxy-2-naphthate]

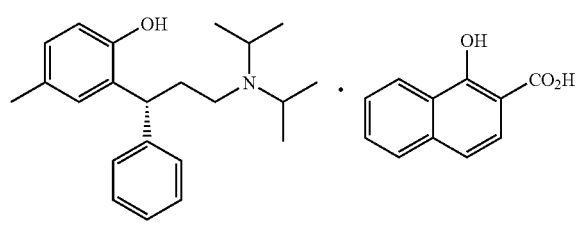

[formula 12: tolterodine glucolate]

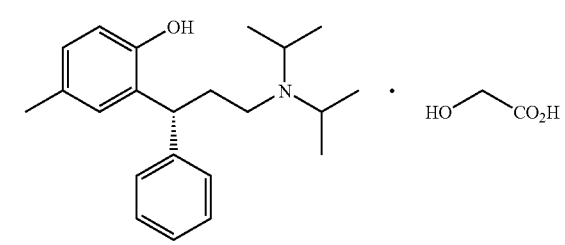

[formula 13: tolterodine retinoate]

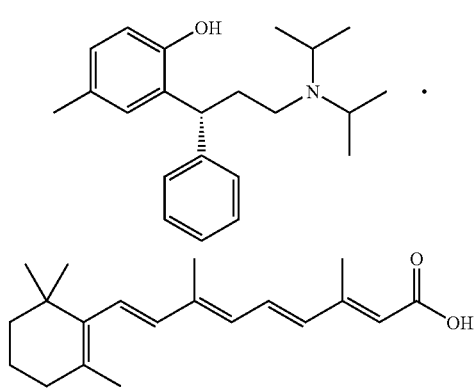

The various novel acid salts of the present invention meet all the following five physicochemical requirements as pharmaceutically acceptable salts.

(1) low hygroscopicity
(2) appropriate solubility
(3) excellent storage stability
(4) convenience in large scale manufacture Therefore, the present invention relates to a pharmaceutical composition for the treatment of overactive bladder comprising the aforementioned various novel acid salts of tolterodine as active ingredient.

The pharmaceutical composition of the present invention can be administered orally or parenterally for clinical trial and may be used in the form of general pharmaceutical formulations. That is, it can be formulated into various preparations for oral or parenteral administration by using a diluent such as a filler, a binder, a wetting agent, a disintegrant, a surfactant or an excipient.

Examples of solid preparations include tablets, pills, powders, granules, capsules, etc.

Examples of the liquid preparation for oral administration include a suspension, an oral liquid, an emulsion, a syrup, etc., and it may comprise various excipients such as a wetting agent, a sweetener, a fragrant, a preservative in addition to the commonly used diluents such as water, liquid paraffin.

Examples of the preparation for parenteral administration include a sterilized aqueous solution, a suspension, an emulsion, a lyophilizer, a suppository, and a patch.

Examples of a non-aqueous solvent or a suspension solvent include propylene glycol, polyethylene glycol, a vegetable oil such as olive oil, an injectable ester such as ethyl oleate.

The base materials to be used for a suppository are Witepsol, Macrogol, Tween 61, cacao oil, glycerogelatin, etc.

The base materials to be used for a patch include various excipients and adhesives to assist its adhesion to skin.

The dosage of the pharmaceutical composition of the present invention to be administered to a patient can vary depending on the patient's age, body weight, administration route, health conditions, and seriousness of the disease(s).

Tolterodine tartrate is orally administered twice daily 2 mg per each administration for the treatment of overactive bladder such as urinary frequency, urinary urgency, and urgent urinary incontinence.

The present invention is described further in detail with reference to the following examples but it should be construed as limiting the scope of the present invention.

Example 1

Preparation of Tolterodine Hippurate 3.25 g of tolterodine dissolved in 50 mL of acetone was mixed at room temperature (25° C.) with 1.79 g of hippuric acid, which was suspended in 50 mL of acetone, and then stirred. Acetone in the above mixture was removed by nitrogen reflux apparatus, and when about 10 20 mL of acetone was removed there started to appear a solid precipitate. After stirring the mixture at room temperature (25° C.) for 1 hour, the solid precipitate was filtered and then washed with hexane. The resultant was dried at room temperature (25° C.) for 24 hours and 4.66 g (theoretical yield: 92.3%) of the final product in white solid was obtained.

Example 2

Preparation of Tolterodine Hemiadipate 3.25 g of tolterodine dissolved in 50 mL of acetone was mixed at room temperature (25° C.) with 0.73 g of adipic acid, which was suspended in 50 mL of acetone, and then stirred. In 10 minutes, there started to appear a solid precipitate. 100 mL of acetone was added thereto and the mixture was stirred at room temperature (25° C.) for 1 hour. The resulting solid precipitate was filtered and then washed with acetone. The resultant was dried at room temperature (25° C.) for 24 hours and 2.96 g (theoretical yield: 74.3%) of the final product in white solid was obtained.

Example 3

Preparation of Tolterodine Gentisate 3.25 g of tolterodine dissolved in 50 mL of acetone was mixed at room temperature (25° C.) with 4.80 g of gentisic acid, which was suspended in 50 mL of acetone, and then stirred. Acetone in the above mixture was removed by nitrogen reflux apparatus, and when about 10 20 mL of acetone was removed there started to appear a solid precipitate. After stirring the mixture at room temperature (25° C.) for 1 hour, the solid precipitate was filtered and then washed with hexane. The resultant was dried at room temperature (25° C.) for 24 hours and 2.04 g (theoretical yield: 42.5%) of the final product in white solid was obtained.

Example 4

Preparation of Tolterodine Benzene Sulfonate 3.25 g of tolterodine dissolved in 50 mL of acetone was mixed at room temperature (25° C.) with 1.58 g of benzenesulfonic acid, which was suspended in 50 mL of acetone, and then stirred. Acetone in the above mixture was removed by nitrogen reflux apparatus. When about 70 80 mL of acetone was removed a mixed solution of diethyl ether and hexane was added thereto and stirred and there started to appear a solid precipitate. After stirring the resulting mixture at room temperature (25° C.) for 1 hour, the solid precipitate was filtered and then washed with hexane. The resultant was dried at room temperature (25° C.) for 24 hours and 4.35 g (theoretical yield: 89.9%) of the final product in white solid was obtained.

Example 5

Preparation of Tolterodine Toluene Sulfonate 3.25 g of tolterodine dissolved in 50 mL of acetone was mixed at room temperature (25° C.) with 1.72 g of p-toluenesulfonic acid, which was suspended in 50 mL of acetone, and then stirred. Acetone in the above mixture was removed by nitrogen reflux apparatus, and when about 70 80 mL of acetone was removed there started to appear a solid precipitate. After stirring the mixture at room temperature (25° C.) for 1 hour, the solid precipitate was filtered and then washed with hexane. The resultant was dried at room temperature (25° C.) for 24 hours and 4.13 g (theoretical yield: 83.0%) of the final product in white solid was obtained.

Example 6

Preparation of Tolterodine L-Pyroglutamate 3.25 g of tolterodine dissolved in 50 mL of acetone was mixed at room temperature (25° C.) with 1.29 g of L-pyroglutamic acid, which was suspended in 50 mL of acetone, and then stirred. In 10 minutes, there started to appear a solid precipitate. 50 mL of acetone was added thereto and the mixture was stirred at room temperature (25° C.) for 1 hour. The resulting solid precipitate was filtered and then washed with acetone. The resultant was dried at room temperature (25° C.) for 24 hours and 3.74 g (theoretical yield: 82.3%) of the final product in white solid was obtained.

Example 7

Preparation of Tolterodine Benzoate 3.25 g of tolterodine dissolved in 50 mL of acetone was mixed at room temperature (25° C.) with 1.22 g of benzoic acid, which was suspended in 50 mL of acetone, and then stirred. In 10 minutes, there started to appear a solid precipitate. 50 mL of acetone was added thereto and the mixture was stirred at room temperature (25° C.) for 1 hour. The resulting solid precipitate temperature (25° C.) for 24 hours and 3.27 g (theoretical yield: 73.1%) of the final product in white solid was obtained.

Example 8

Preparation of tolterodine hemi naphthalene-1,5-disulfonate 3.25 g of tolterodine dissolved in 50 mL of acetone was mixed at room temperature (25° C.) with 1.44 g of naphthalene-1,5-disulfonic acid, which was suspended in 50 mL of acetone, and then stirred. In 10 minutes, there started to appear a solid precipitate. 50 mL of acetone was added thereto and the mixture was stirred at room temperature (25° C.) for 1 hour. The resulting solid precipitate was filtered and then washed with acetone. The resultant was dried at room temperature (25° C.) for 24 hours and 3.68 g (theoretical yield: 78.4%) of the final product in white solid was obtained.

Example 9

Preparation of tolterodine 1-hydroxy-2-naphthate 3.25 g of tolterodine dissolved in 50 mL of acetone was mixed at room temperature (25° C.) with 1.88 g of 1-hydroxy-2-naphthoic acid, which was suspended in 50 mL of acetone, and then stirred for 30 minutes. Acetone in the above mixture was removed by nitrogen reflux apparatus, and when about 10~20 mL of acetone was removed there started to appear a solid precipitate. After stirring the mixture at room temperature (25° C.) for 1 hour, the solid precipitate was filtered and then washed with hexane. The resultant was dried at room temperature (25° C.) for 24 hours and 4.32 g (theoretical yield: 84.1%) of the final product in light brown solid was obtained.

Example 10

Preparation of Tolterodine Glucolate 3.25 g of tolterodine dissolved in 50 mL of acetone was mixed at room temperature (25° C.) with 0.76 g of glycolic acid, which was suspended in 50 mL of acetone, and then stirred. In 10 minutes, there started to appear a solid precipitate. 50 mL of acetone was added thereto and the mixture was stirred at room temperature (25° C.) for 1 hour. The resulting solid precipitate was filtered and then washed with acetone. The resultant was dried at room temperature (25° C.) for 24 hours and 2.78 g (theoretical yield: 69.2%) of the final product in white solid was obtained.

Example 11

Preparation of Tolterodine Retinoate 3.25 g of tolterodine dissolved in 15 mL of acetone was mixed at room temperature (25° C.) with 3.0 g of retinoic acid, which was suspended in 15 mL of acetone, and then stirred. In 10 minutes, 30 mL of ethanol was added thereto to completely dissolve the mixture. In an hour there started to appear a solid precipitate) and the mixture was stirred at room temperature (25° C.) for 12 hours. The resulting solid precipitate was filtered and then washed with acetone. The resultant was dried at room temperature (25° C.) for 24 hours and 1.40 g (theoretical yield: 22.4%) of the final product in yellow solid was obtained.

Example 12

Formulation of a Transdermal Patch Comprising an Acid Salt of Tolterodine 0.5 g of tolterodine toluene sulfonate manufacture in the above Example 5 was dissolved in 7 mL of ethanol, added with 3 mL of propylene glycol and 3 mL of isopropyl palmitate, and then added with 25 g of Durotak 87-2287 (National Starch) as an acrylic adhesive, and placed at room temperature for abut 24 hours to remove foams. The resultant was coated onto the silicon-coated PET release film with 600 μm of thickness by using an automatic coater, allowed to dry at 80° C. for 20 minutes, laminated the PET backing film by covering with it. Thus obtained product was cut by using a rectangular cutter to finally prepare a transdermal patch.

Example 13

Formulation of a Capsule Comprising an Acid Salt of Tolterodine

Microcrystalline cellulose (525 g, 90 μm) and dried corn starch were premixed. Part of the premix was then added with an acid salt of tolterodine (70 g) selected from the compounds of the following formulas 1-13 and the mixture was sieved. Then, the remaining premix was added thereto and mixed for 10 minutes, sieved and then mixed for additional 5 minutes. The resultant was filled into an appropriate size of a capsule to obtain a capsule preparation.

Example 14

Formulation of an Injection Comprising an Acid Salt of Tolterodine

Sodium chloride was dissolved in sterile water for injection and mixed with propylene glycol. An acid salt of tolterodine selected from the compounds of the following formulas 1-13 was added to the mixture. Upon dissolution, the sterile water for injection was added thereto to manufacture a solution with target concentration. The solution was filtered through a sterile filter and then filled into a sterile ampoule for injection container.

Test Example 1

Stability Test

This experiment is designed to confirm the storage stability of the various acid salts of tolterodine.

For a pharmaceutical drug to be processed into a certain formulation it is essential to be provided with sufficient storage stability. For example, for tablets or capsules, it is necessary for them to have stability in atmospheric condition, for injections, stability in moisture (water), and for patches, both stability in atmospheric condition and in moisture (water).

The following Table 1 shows comparative stability test results under oxidation condition, where tolterodine tartrate and a novel acid salt of tolterodine were dissolved in 0.3% hydrogen peroxide solution, placed at room temperature for 24 hours and the area ratio of the total related substances was quantitated with HPLC.

Further, the Table 1 shows comparative test results for alkali stability, where tolterodine tartrate and a novel acid salt of tolterodine were dissolved in 1M sodium hydroxide solution, placed at room temperature for 24 hours and the area ratio of the total related substances was quantitated with HPLC.

TABLE 1

Stability Test of Acid Salt of Tolterodine [Total impurities: % area]

| material | Condition | | |
|---|---|---|---|
| | oxidation | acid | alkali |
| tolterodine hippurate | 0.41 | 0.11 | 0.14 |
| tolterodine hemiadipate | 0.39 | 0.14 | 0.10 |
| tolterodine gentisate | 0.23 | 0.03 | 0.04 |
| tolterodine benzenesulfonate | 0.51 | 0.02 | 0.08 |
| tolterodine p-toluenesulfonate | 0.09 | 0.11 | 0.06 |
| tolterodine L-pyroglutamate | 0.56 | 0.03 | 0.08 |
| tolterodine benzoate | 0.39 | 0.02 | 0.10 |
| tolterodine hemi naphthalene-1,5-disulfonate | 0.40 | 0.07 | 0.11 |
| tolterodine 1-hydroxy-2-naphtate | 0.33 | 0.10 | 0.15 |
| tolterodine glucolate | 0.44 | 0.11 | 0.23 |
| tolterodine retinoate | 0.08 | 0.15 | 0.19 |
| tolterodine tartrate (control) | 0.98 | 0.20 | 0.29 |
| tolterodine free base | 4.74 | 0.59 | 0.83 |

Ð

As shown in the above Table 1, the various novel acid salts of tolterodine, as compared with the conventional free base or tolterodine tartrate, were shown to have excellent storage stability under oxidation condition, and in the presence of an acid and a base.

Test Example 2

Measurement of Cumulative Amount after In Vitro Penetration Test

A conventional tolterodine tartrate and a novel acid salt of tolterodine were dissolved or dispersed in propylene glycol to a final concentration of 10 mg/mL. 1 mL of tolterodine salt was added onto a Frantz cell, which was mounted with a hairless mouse skin. Then, the amount of tolterodine penetrated through the skin at 32° C. was quantitated and its cumulative amount was measured.

TABLE 2

| Category (unit μg) | Time (hr) | | | | |
|---|---|---|---|---|---|
| | 0 | 3 | 6 | 9 | 12 |
| tolterodine hippurate | 0.0 | 0.0 | 0.0 | 0.8 | 2.8 |
| tolterodine hemiadipate | 0.0 | 0.0 | 3.4 | 5.9 | 14.8 |
| tolterodine gentisate | 0.0 | 0.0 | 0.4 | 1.3 | 2.8 |
| tolterodine benzenesulfonate | 0.0 | 0.0 | 0.4 | 0.8 | 1.7 |
| tolterodine p-toluenesulfonate | 0.0 | 1.1 | 8.0 | 19.9 | 36.6 |
| tolterodine L-pyroglutamate | 0.0 | 1.3 | 2.4 | 2.1 | 3.3 |
| tolterodine benzoate | 0.0 | 3.2 | 5.5 | 8.6 | 13.2 |
| tolterodine hemi naphthalene-1,5-disulfonate | 0.0 | 3.6 | 2.4 | 1.7 | 1.8 |
| tolterodine 1-hydroxy-2-naphtate | 0.0 | 0.6 | 0.7 | 1.3 | 2.2 |
| tolterodine glucolate | 0.0 | 1.2 | 4.7 | 5.1 | 8.3 |
| tolterodine retinoate | 0.0 | 0.5 | 1.7 | 2.5 | 4.1 |
| tolterodine tartrate (control) | 0.0 | 0.0 | 0.0 | 0.0 | 0.0 |

As stated above, the various novel acid salts of tolterodine according to the present invention show that they are acid salts which are more suitable for the manufacture of a transdermal drug delivery system as compared to the conventional tolterodine tartrate, and are expected to be used for a pharmaceutical composition for the treatment of overactive bladder.

INDUSTRIAL APPLICABILITY

The present invention provides a method of efficient transdermal delivery of a pharmaceutical drug such as various acid salts of tolterodine from liquid amorphous tolterodine free base and the novel pharmaceutical compounds obtained thereof by using various formulation methods.

The invention claimed is:

1. An acid salt of Tolterodine selected from the group consisting of:

Tolterodine hippurate represented by the following formula 3;

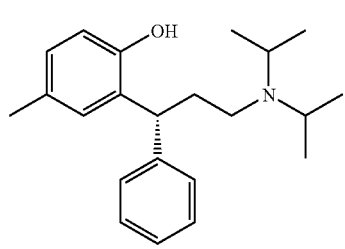

[formula 3]

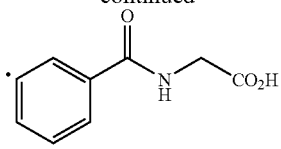

Tolterodine gentisate represented by the following formula 5;

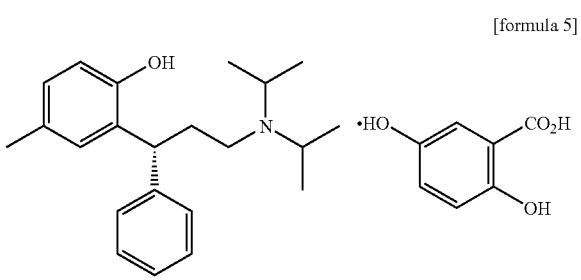

[formula 5]

Tolterodine benzene sulfonate represented by the following formula 6;

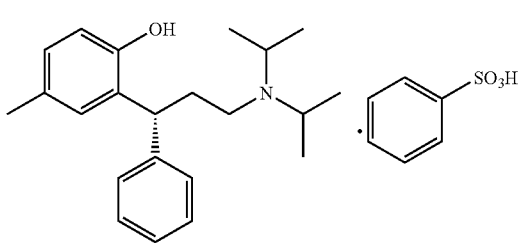

[formula 6]

Tolterodine p-toluene sulfonate represented by the following formula 7;

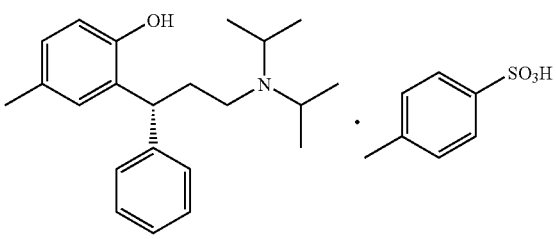

[formula 7]

Tolterodine L-pyroglutamate represented by the following formula 8;

[formula 8]

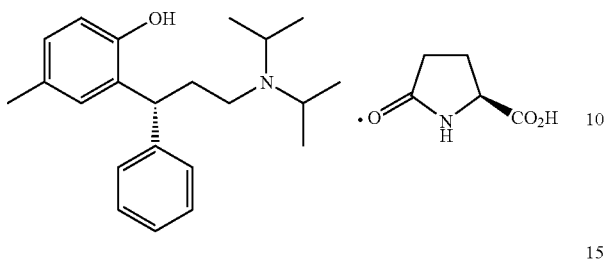

Tolterodine hemi naphthalene-1,5-disulfonate represented by the following formula 10;

[formula 10]

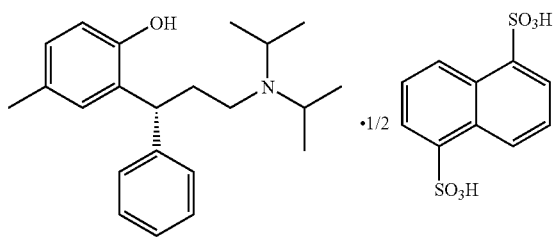

and;
Tolterodine glucolate represented by the following formula 12;

[formula 12]

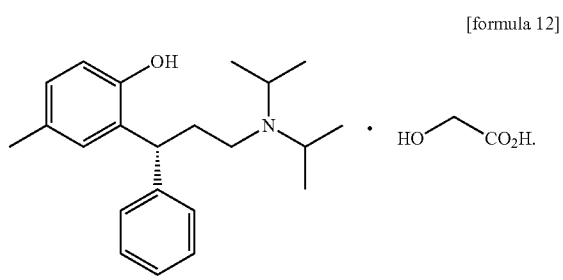 [SMILES: Cc1ccc(O)c([C@H](CCN(C(C)C)C(C)C)c2ccccc2)c1 ; O=C(O)CO]

2. A pharmaceutical composition comprising a pharmaceutically effective amount of the acid salt of claim 1 as an active ingredient for the treatment of overactive bladder and a pharmaceutically acceptable diluent or excipient.

3. A transdermal drug delivery system comprising a pharmaceutically effective amount of the acid salt of claim 1 as an active ingredient for the treatment of overactive bladder.

* * * * *